United States Patent [19]

Gerster

[11] 3,984,548

[45] Oct. 5, 1976

[54] SUBSTITUTED PYRIDO[1,2,3-de]-1,4-BENZOXAZINES AS BACTERICIDES

[75] Inventor: John F. Gerster, Woodbury Township, Washington County, Minn.

[73] Assignee: Riker Laboratories, Inc., Northridge, Calif.

[22] Filed: Nov. 21, 1974

[21] Appl. No.: 525,726

Related U.S. Application Data

[60] Division of Ser. No. 440, 951, Feb. 11, 1974, Pat. No. 3,883,522.

[52] U.S. Cl. .............................................. 424/248
[51] Int. Cl.[2] ................. A61K 31/535; A61L 13/00
[58] Field of Search ..................... 260/244; 424/248

[56] References Cited

UNITED STATES PATENTS 3,055,894   9/1962   Lombardino et al. ............... 424/248
3,551,565   12/1970   Clarke ............................... 424/248

OTHER PUBLICATIONS

Chem. Abst. 72 90686(s) (1970), Teacher et al.

*Primary Examiner*—Sam Rosen
*Assistant Examiner*—D. W. Robinson
*Attorney, Agent, or Firm*—Alexander, Sell, Steldt & DeLaHunt

[57] ABSTRACT

Anti-microbial agents which are 2,3-dihydro-3-substituted-7-oxo-pyrido[1,2,3-de]-1,4-benzoxazine-6-carboxylic acids are prepared by condensation of benzoxazines with ethoxymethylene malonate esters followed by ring closure with poly phosphoric acid and hydrolysis of the resulting esters.

10 Claims, No Drawings

SUBSTITUTED PYRIDO[1,2,3,-de]-1,4-BENZOXAZINES AS BACTERICIDES

BACKGROUND OF THE INVENTION

This is a division of application Ser. No. 440,951 filed, Feb. 11, 1974, now U.S. Pat. No. 3,883,522.

This invention relates to derivatives of the heterocyclic system known as pyrido[1,2,3-de]benzoxazine. More specifically, it relates to 2,3-dihydro-3-substituted-7-oxo-7H-pyrido[1,2,3-de]-1,4-benzoxazine-6-carboxylic acids, their salts and esters thereof. These compounds are optionally substituted at the 3 (three) position by lower alkyl groups and on the benzo ring portion by a variety of substituents. A further aspect of this invention relates to the use of these compounds as anti-microbial agents in pharmaceutically acceptable compositions.

DESCRIPTION OF THE PRIOR ART

The basic ring structure of pyrido[1,2,3-de]-1,4-benzoxazine is known. Fischer, Ber. 16,712 (1883), reports a compound with the structure 2-oxo-3,6,7-trihydro-5H-pyrido[1,2,3-de]-1,4-benzoxazine. The compound 2,3,6,7-tetrahydro-5H-pyrido[1,2,3-de]-1,4-benzoxazine is reported by Isler, Helv. Chim. Acta 27,1756 (1944). Dickey and McNally (U.S. Pat. No. 2,448,869) list a number of compounds as intermediates having the same basic ring structure which they name as trimethylenebenzomorpholines. The compounds of this invention differ from and are not believed to be suggested or anticipated by any of these known compounds.

This invention relates to derivatives of 2,3-dihydro-7-oxo-7H-pyrido[1,2,3-de]-1,4-benzoxazine. The structure and numbering method for this heterocyclic ring system are shown below:

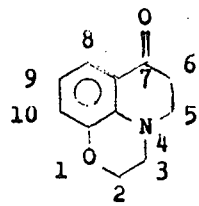

The compounds of the invention are represented by the following structural formula:

Formula I 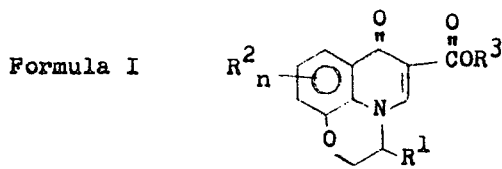

wherein $R^3$ is hydrogen, a cation or lower alkyl, $R^1$ is hydrogen or lower alkyl, $R^2$ is lower alkyl, lower alkoxy, halogen or nitro, n is zero to three and when $R^2$ is nitro, $R^1$ is methyl or ethyl.

"Lower alkyl" or "lower alkoxy" as used herein means alkyl or alkoxy, respectively, having from 1 to 4 carbon atoms in straight or branched chain configuration.

Compounds of the invention wherein $R^3$ is hydrogen, which are acids, are preferred as anti-microbial agents. Salts of said acids are equivalent to the acids. Compounds wherein $R^3$ is lower alkyl are primarily useful as intermediates for the preparation of the corresponding acids, although some of these compounds also exhibit anti-microbial activity.

Cations as defined herein are pharmaceutically acceptably cations which form salts with the compounds wherein $R^3$ is hydrogen, such as alkali metal, alkaline earth, aluminum, iron and other metal and amine salts. Such pharmaceutically acceptable salts are known to be equivalent to the acids for many purposes, and may even offer advantages in absorption, formulation and the like.

The anti-microbial activity of these compounds can be demonstrated by the standard plate dilution method for bacterial susceptibility of antibiotics, (English Antibiot. Chemother. Vol. 1, 118, 1951). The culture medium employed permits susceptibility testing of fastidious microorganisms towards antibiotics, sulfonamides and other chemotherapeutic agents. Tryptone soy agar (oxoid) of the following composition is the culture medium.

| | |
|---|---|
| Oxoid tryptone | 15 g |
| Oxoid soypeptone | 5 g. |
| Sodium chloride | 5 g. |
| Oxoid agar-agar No. 3 | 15 g. |
| Water | 1 liter |

Using this test, the compounds of the invention have been found to have a broad spectrum of activity against gram-positive and gram-negative microorganisms.

The compounds of the invention are active against microorganisms either in the absence or presence of ten percent horse serum.

In the test procedure, the amount of a compound required to give complete inhibition or no inhibition of the microbial growth on the agar plates was determined. The compound selected for evaluation is added to the agar medium to give concentrations of one, ten and one hundred milligrams per liter. A series of plates with these concentrations is prepared. Plates containing agar alone are included as controls. Ten percent horse serum is added to one series of such plates. Aliquots of broth culture of each of nine species of microorganisms are innoculated onto the agar plates containing the various compound concentrations and onto the control plates. The plates are incubated at 37° C. in a 10 percent carbon dioxide atmosphere for 18 to 25 hours. The microbial growth on each plate is read visually, and minimal inhibitory concentrations are recorded.

The microorganisms used for this test were:
1. Staphylococcus aureus
2. Bacillus subtilus
3. Pseudomonas aeruginosa
4. Escherichia coli
5. streptococcus sp.*
6. Aspergillus niger
7. Candida albicans
8. Mima polymorpha
9. Herellea vaginicola

*Strains isolated from dental caries in rats or hamsters at the National Institute of Dental Health and grown in PFY or APT agar.

All of the compounds of the invention either possess antibacterial activity towards one or more of the above microorganisms, or are useful intermediates in the preparation of compounds which exhibit such activity.

Many of the compounds of the invention have also shown activity versus anaerobic bacteria, for example *Bacteroides* sp. and *Clostridium welchii*. Some compounds have shown activity versus *Erwinia amylovora*, a gram-negative microorganism responsible for the plant disease known as fire blight.

It will be understood by those skilled in the art that the species used are representative indicator species, as it would be impractical to screen against all bacteria. It is well known in the art that broad spectrum activity can be predicted on the activity shown against selected representative bacterial species.

All of the compounds of the invention are active versus microorganisms in vitro or topically. In vitro activity is useful in itself, since anti-microbial agents may be used for disinfecting and sterilizing, for example medical and dental equipment, as components of disinfecting solutions. The preferred compounds of the invention are also active in vivo in animals. These compounds exhibit anti-microbial activity when administered orally to animals. They are excreted in the urine and are effective antibacterial agents for treatment of urinary tract infections in mammals.

the acute oral toxicity of the compounds of the invention is generally moderate to low compared with the effective oral dose, and they have a fair to excellent therapeutic ratio.

Presently preferred compounds of the invention have a broad spectrum of anti-microbial activity and a good therapeutic ratio ($LD_{50}/ED_{50}$).

These compounds are:
2,3-dihydro-10-fluoro-3-methyl-7-oxo-7H-pyrido[1,2,3-de]-1,4-benzoxazine-6-carboxylic acid
10-chloro-2,3-dihydro-3-methyl-7-oxo-7H-pyrido[1,2,3-de]-1,4-benzoxazine-6-carboxylic acid
2,3-dihydro-9-fluoro-7-oxo-7H-pyrido[1,2,3-de]-benzoxazine-6-carboxylic acid
9-chloro-2,3-dihydro-3-methyl-7-oxo-7H-pyrido[1,2,3-de]-1,4-benzoxazine-6-carboxylic acid
10-chloro-2,3-dihydro-3,8-dimethyl-7-oxo-7H-pyrido[1,2,3-de]-1,4-benzoxazine-6-carboxylic acid
2,3-dihydro-3,10-dimethyl-7-oxo-7H-pyrido[1,2,3-de]-1,4-benzoxazine-6-carboxylic acid
9-chloro-2,3-dihydro-3,10-dimethyl-7-oxo-7H-pyrido-[1,2,3-de]-1,4-benzoxazine-6-carboxylic acid
2,3-dihydro-7-oxo-3,8,10-trimethyl-7H-pyrido[1,2,3-de]-1,4-benzoxazine-6-carboxylic acid
2,3-dihydro-3,9-dimethyl-7-oxo-pyrido[1,2,3-de]-1,4-benzoxazine-6-carboxylic acid and salts thereof.

The compounds of the invention may be formulated by incorporating them into conventional pharmaceutical carrier materials, either organic or inorganic, for example, in formulating tablets or capsules for oral administration or liquid preparations suitable, for example, for intraperitoneal application. For in vitro or topical use, simple aqueous solutions or suspensions are most conveniently employed. For this purpose, concentrations of the order of 100 parts per million up to 5 parts per thousand are suitable. The formulation is used by immersing objects to be treated therein, or by local application to an infected area.

The amount of compound to be used, for example, in the treatment of a urinary tract infection by oral administration, will be an effective amount less than a toxic amount. The amount administered to control the infection will depend on the species, sex, weight, and physical condition of the patient as well as other variable factors. This judgment is well within the skill of the medical art. Usually the amount will be less than 100 mg/kg. per dose. Conveniently this is administered in the form of ordinary pharmaceutical preparations such as capsules, tablets, emulsions, solutions and the like. Excipients, fillers, coatings, etc. are usually employed with tablets or capsules, as is well known in the art.

It is known to the art that anti-microbial agents are used as growth promoters in various animal and bird species. Although not yet verified, it can be inferred from their antimicrobial activity that the compounds of this invention can be used for this purpose also. The compounds of the invention may also be useful for the control of microbial (e.g. *Erwinia amylovora*) infections of plants, e.g. by spraying or dusting formulatons of these compounds on the affected area.

Compounds of the invention are prepared by the following reaction sequence:

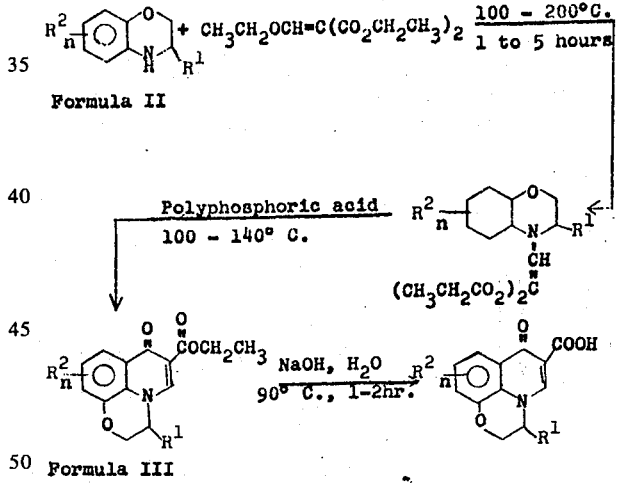

Formula II

Formula III

In the above reaction sequence a dialkyl ethoxymethylene malonate (illustrated by diethyl ethoxymethylene malonate) is condensed with a 3,4-dihydro-2H-1,4-benzoxazine of Formula II by heating without solvent at 100° to 200° C. for one to five hours. The novel intermediates thus formed are generally oils which need not be purified for further use in the reaction. Polyphosphoric acid is then added and the solution is heated to 100° to 140° C. to effect a condensation to the novel intermediates of Formula III. The compounds of Formula III are included within the scope of the invention as useful intermediates in the preparation of compounds of Formula I. The final step is saponification of the esters of Formula III to the acids of Formula I.

Compounds of Formula II are generally known, or may be prepared by procedures known to the art. For example, see U.S. Pat. No. 2,448,869. Compounds of Formula II may be conveniently prepared by one of the following methods:

Procedure A

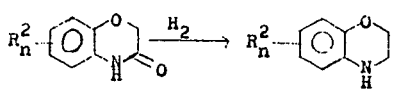

wherein $R^2$ and n are as defined hereinabove.

Procedure B

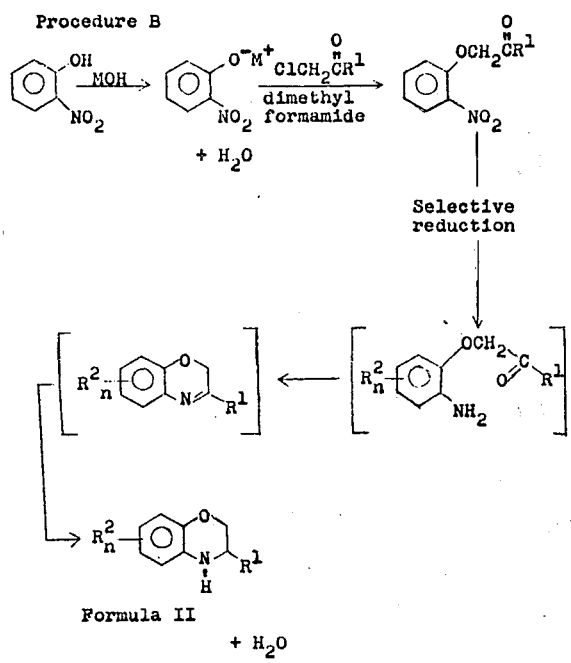

Formula II wherein $R^2$ and n are as defined hereinabove, M is an alkali metal and $R^1$ is lower alkyl.

In procedure A chemical reduction methods using diborane or metal hydrides provide intermediates wherein $R^1$ is hydrogen.

In procedure B, comprising several known reactions, step 1 is the formation of phenolate salt of ortho-nitrophenol and step 2 is the displacement of halogen (illustrated by chlorine) of a halomethyl lower alkyl ketone. Step 3 requires selective hydrogenation of the nitro group by catalytic methods, for example using palladium on charcoal or Raney nickel, or chemical methods, for example, iron and acetic acid. This hydrogenation is followed by spontaneous cyclization of the resulting aniline and further reduction to a compound of Formula II.

Some compounds of the invention wherein $R^2$ is nitro may also be prepared by direct nitration of other compounds of the invention.

The following non-limiting examples are provided to illustrate the compounds of the invention and synthetic methods useful to obtain them.

EXAMPLE 1

Diethyl ethoxymethylene malonate (19.8 g., 0.092 mole) is added to 3,4-dihydro-3,7-dimethyl-2H-1,4-benzoxazine (15.0 g., 0.092 mole) and the solution is heated at 110° to 120° C. for three hours. Polyphosphoric acid (100 g.) is added and the solution is gradually heated to 130° C. with occasional stirring. The solution is heated at 140° to 150° C. for one additional hour. The hot solution is poured into 300 ml. water with stirring, then neutralized with forty percent sodium hydroxide solution. The solid which precipitates is separated by filtration and washed with water. Recrystallization from ethanol gives ethyl 2,3-dihydro-3,9-dimethyl-7-oxo-7H-pyrido[1,2,3-de]-1,4-benzoxazine-6-carboxylate, m.p. 195°–197° C.

| Analysis: | %C | %H | %N |
|---|---|---|---|
| Calculated for $C_{16}H_{17}NO_4$: | 66.9 | 6.0 | 4.9 |
| Found: | 66.4 | 5.9 | 4.9 |

EXAMPLE 2

Using the method of Example 1 diethyl ethoxymethylene malonate is reacted with 3,4-dihydro-6-methoxy-3-methyl-2H-1,4-benzoxazine and the product reacted with polyphosphoric acid to provide ethyl 2,3-dihydro-8-methoxy-3-methyl-7-oxo-7H-pyrido[1,2,3-de]-1,4-benzoxazine-6-carboxylate, m.p. 165°–168° C.

EXAMPLE 3

Using the method of Example 1, diethyl ethoxymethylene malonate is reacted with 6-chloro-3,4-dihydro-3-methyl-2H-1,4-benzoxazine and the product reacted with polyphosphoric acid to provide ethyl 8-chloro-2,3-dihydro-3-methyl-7-oxo-7H-pyrido[1,2,3-de]-1,4-benzoxazine-6-carboxylate, m.p. 205°–206° C.

Additional compounds prepared using the method of Example 1 are:

Example No.

4  ethyl 9-chloro-2,3-dihydro-3-methyl-7-oxo-7H-pyrido[1,2,3-de]-1,4-benzoxazine-6-carboxylate, m.p. 236°–238° C.

5  ethyl 2,3-dihydro-8-fluoro-3-methyl-7-oxo-7H-pyrido[1,2,3-de]-1,4-benzoxazine-6-carboxylate, m.p. 235°–237° C.

6  ethyl 2,3-dihydro-9-fluoro-3-methyl-7-oxo-7H-pyrido[1,2,3-de]-1,4-benzoxazine-6-carboxylate, m.p. 223°–225° C.

The following compounds are prepared using the method of Example 1 by reacting 8-chloro-3,4-dihydro-3-methyl-2H-1,4-benzoxazine with various esters of ethoxymethylene malonate as shown:

TABLE I

| Example No. | Ethoxy-methylene malonate ester | Product of Formula I |
|---|---|---|
| 7 | methyl | 7-chloro, methyl ester structure with $CO_2CH_3$ and $CH_3$ |
| 8 | n-butyl | 7-chloro, n-butyl ester structure with $CO_2CH_2CH_2CH_2CH_3$ and $CH_3$ |
| 9 | isopropyl | 7-chloro, isopropyl ester structure with $CO_2CH(CH_3)_2$ and $CH_3$ |
| 10 | n-hexyl | 7-chloro, n-hexyl ester structure with $CO_2(CH_2)_5CH_3$ and $CH_3$ |

The following compounds are prepared using the method of Example 1 by reacting diethyl ethoxymethylene malonate with various 1,4-benzoxazines as shown:

TABLE II

| Example No. | 1,4-Benzoxazine | Product of Forumula I |
|---|---|---|
| 11 | benzoxazine with $CH_2CH_3$ and NH | product with $CO_2CH_2CH_3$ and $CH_2CH_3$ |
| 12 | Cl-substituted benzoxazine with $CH_2CH_2CH_3$ and NH | Cl-substituted product with $CO_2CH_2CH_3$ and $CH_2CH_2CH_3$ |

TABLE II continued

| Example No. | 1,4-Benzoxazine | Product of Formula I |
|---|---|---|
| 13 | 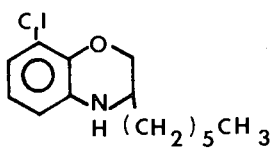 | 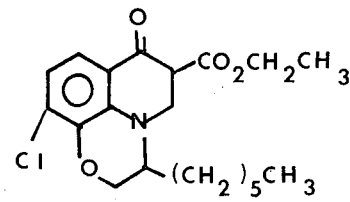 |
| 14 | 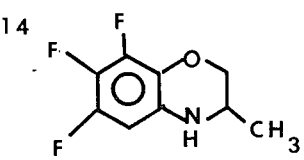 | 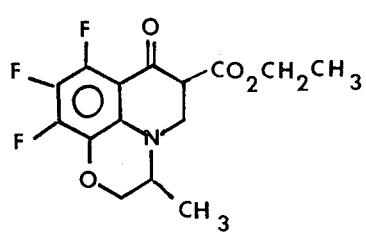 |
| 15 | 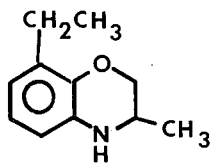 | 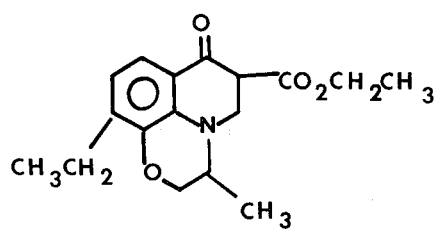 |

EXAMPLE 16

Ethyl 2,3-dihydro-3,9-dimethyl-7-oxo-7H-pyrido[1,2,3-de]-1,4-benzoxazine-6-carboxylate is dissolved in excess three percent sodium hydroxide and heated on the steam bath for one hour. The solution of the sodium salt of 2,3-dihydro-3,9-dimethyl-7-oxo-7H-pyrido[1,2,3-de]-1,4-benzoxazine-6-carboxylate is treated with decolorizing charcoal, filtered, then neutralized with concentrated hydrochloric acid. The off-white solid precipitate is separated by filtration, washed with water and dried. Recrystallization of 2,3-dihydro-3,9-dimethyl-7-oxo-7H-pyrido[1,2,3-de]-1,4-benzoxazine-6-carboxylic acid from dimethyl formamide gives a white solid, m.p 246°–248° C.

| Analysis: | %C | %H | %N |
|---|---|---|---|
| Calculated for $C_{14}H_{13}NO_4$: | 64.9 | 5.1 | 5.4 |
| Found: | 63.8 | 4.7 | 5.3 |

Using the method of Example 16 the following table illustrates compounds of Formula I which were prepared by hydrolysis of compounds wherein $R^3$ is ethyl.

TABLE III

| Example No. | Product Compound | Melting Point (in °C.) |
|---|---|---|
| 17 | 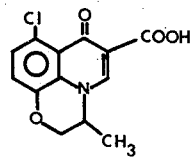 | 290–291°C. |
| | 8-chloro-2,3-dihydro-3-methyl-7-oxo-7H-pyrido[1,2,3-de]-1,4-benzoxazine-6-carboxylic acid | |
| 18 | 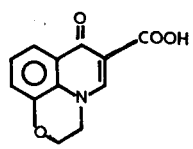 | 299–305 |

TABLE III-continued

| Example No. | Product Compound | Melting Point (in °C.) |
|---|---|---|
| 19 | 2,3-dihydro-7-oxo-7H-pyrido[1,2,3-de]-1,4-benzoxazine-6-carboxylic acid | 235–237 |
| 20 | 2,3-dihydro-3-methyl-7-oxo-7H-pyrido[1,2,3-de]-1,4-benzoxazine-6-carboxylic acid | 236–238 |
| 21 | 2,3-dihydro-9-methoxy-3-methyl-7-oxo-7H-pyrido[1,2,3-de]-1,4-benzoxazine-6-carboxylic acid | 270–273 |
| 22 | 2,3-dihydro-10-fluoro-3-methyl-7-oxo-7H-pyrido[1,2,3-de]-1,4-benzoxazine-6-carboxylic acid | 300–303 |
| 23 | 10-chloro-2,3-dihydro-3-methyl-7-oxo-7H-pyrido[1,2,3-de]-1,4-benzoxazine-6-carboxylic acid | 283–285 |
| 24 | 9-chloro-2,3-dihydro-3-methyl-7-oxo-7H-pyrido[1,2,3-de]-1,4-benzoxazine-6-carboxylic acid | 260–262 |
| 25 | 9-fluoro-2,3-dihydro-3-methyl-7-oxo-7H-pyrido[1,2,3-de]-1,4-benzoxazine-6-carboxylic acid | 249–252 |
| 26 | 8-fluoro-2,3-dihydro-3-methyl-7-oxo-7H-pyrido[1,2,3-de]-1,4-benzoxazine-6-carboxylic acid | 195–197 |
|  | 8-methyl-2,3-dihydro-3-methyl-7-oxo-7H-pyrido[1,2,3-de]-1,4-benzoxazine-6-carboxylic acid |  |

The following table shows compounds which are prepared using the method of Example 16 by hydrolysis of the corresponding ester of Table II hereinabove:

TABLE IV

| Example No. | Product of Formula I |
|---|---|
| 27 | 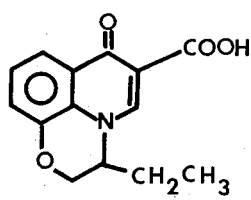 |
| 28 | 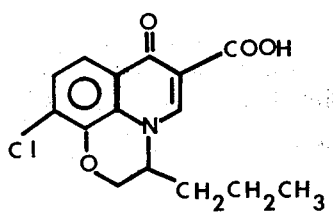 |

TABLE IV continued
| Example No. | Product of Formula I |
|---|---|
| 29 | 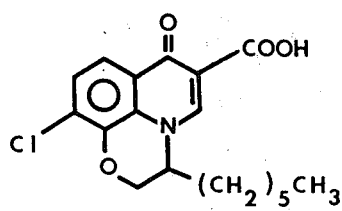 |
| 30 | 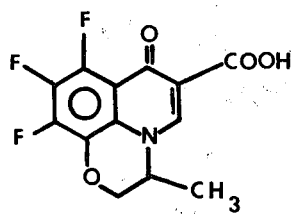 |
| 31 | 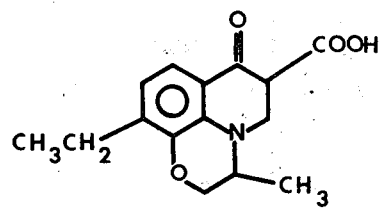 |
The ester starting materials of the following are prepared from the corresponding benzoxazines using the method of Example 1. The acid products of Table V are prepared by hydrolysis of the esters using the method of Example 16.
TABLE V
| Example No. | Ester Starting Material | Acid Product |
|---|---|---|
| 32 | 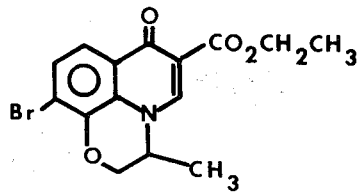 | 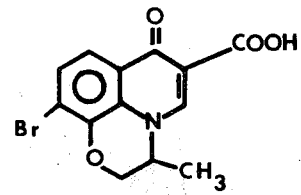 m.p. > 300° C. |
| 33 | 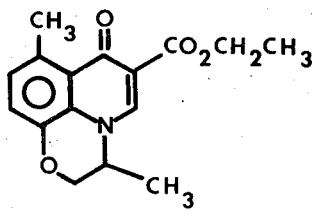 m.p. 140–142° C. | 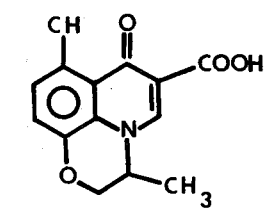 m.p. 195–197° C. |
| 34 | 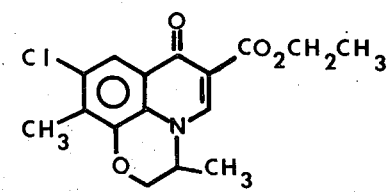 m.p. 284–286° C. | 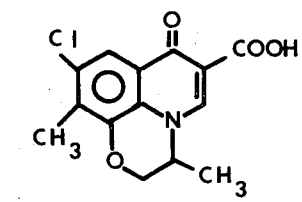 m.p. > 300° |

TABLE V (continued)
| Example No. | Ester Starting Material | Acid Product |
|---|---|---|
| 35 | 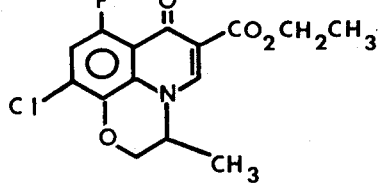 m.p. 219–221° C. | 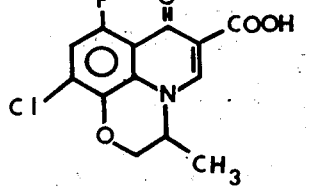 m.p. > 300° C. |
| 36 | 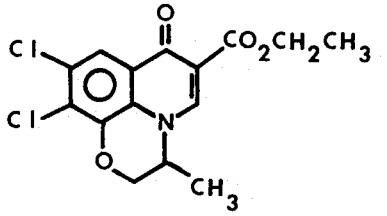 m.p. 285–287° C. | 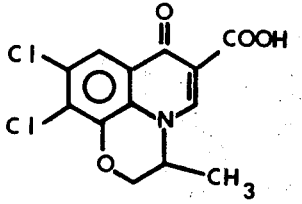 m.p. > 300° C. |
| 37 | 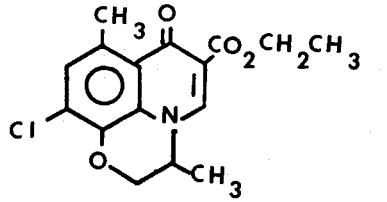 m.p. 199–201° C. | 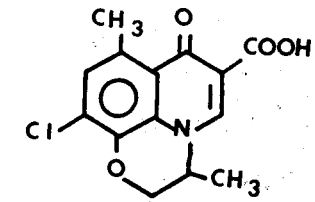 m.p. 245–247° C. |
| 38 | 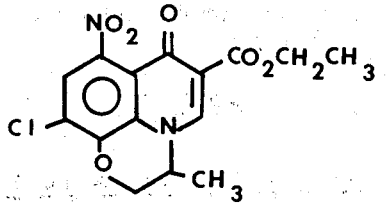 | 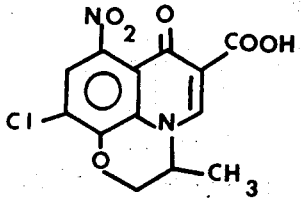 m.p. > 300° C. |
| 39 | 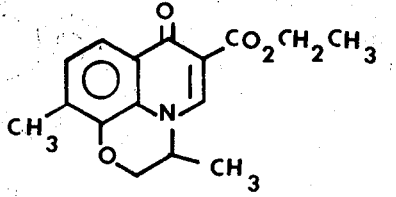 m.p. 202–204° C. | 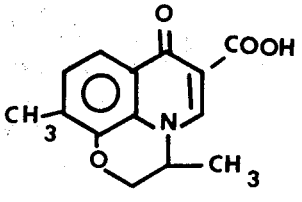 m.p. 271–273° C. |
| 40 | 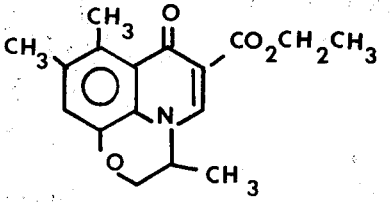 m.p. 195–197° C. | 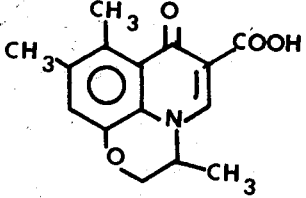 m.p. 247–249° C. |
| 41 | 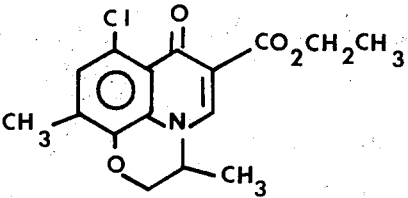 m.p. 243–245° C. | 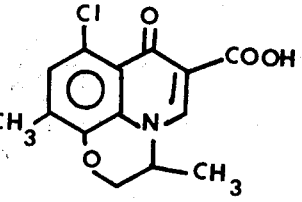 m.p. > 300° C. |

TABLE V (continued)

| Example No. | Ester Starting Material | Acid Product |
|---|---|---|
| 42 | 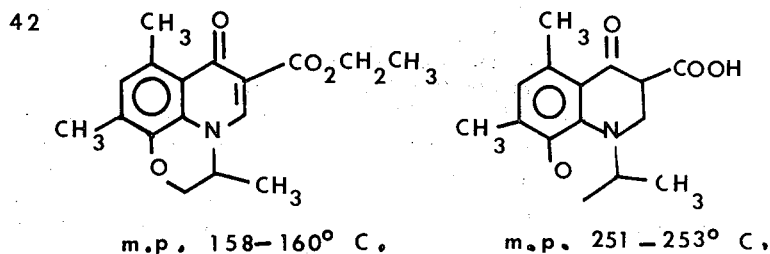 m.p. 158–160° C. | m.p. 251–253° C. |
| 43 | 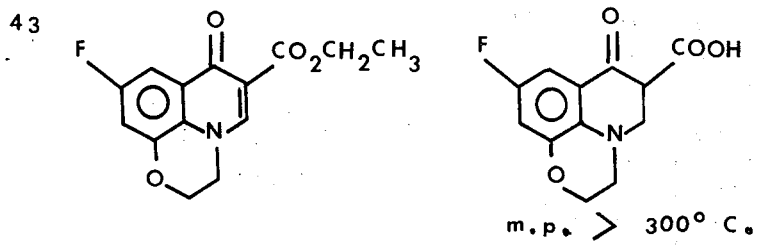 | m.p. > 300° C. |

EXAMPLE 44

2,3-Dihydro-3-methyl-7-oxo-7H-pyrido[1,2,3-de]-1,4-benzoxazine-6-carboxylic acid (3.0 g., 0.072 mole) is dissolved in concentrated sulfuric acid (30 ml.) and the solution is cooled to 0° C. with an ice-salt bath. A mixture of concentrated (70%) nitric acid (0.77 g.) in concentrated sulfuric acid (3 ml.) is added dropwise with stirring while maintaining the reaction temperature at 0° to 5° C. The mixture is allowed to warm to room temperature, then poured, with stirring, over ice. The pH of the solution is adjusted by the addition of concentrated ammonium hydroxide to about 1 to 2. The brown solid is separated by filtration, washed with water and recrystallized from a dimethyl formamide-water mixture. The 2,3-dihydro-3-methyl-8-nitro-7-oxo-7H-pyrido[1,2,3-de]-1,4-benzoxazine-6-carboxylic acid is a tan solid, m.p. 269°–271° C.

| Analysis: | %C | %H | %N |
|---|---|---|---|
| Calculated for $C_{13}H_{10}N_2O_6$: | 53.8 | 3.45 | 9.65 |
| Found: | 54.6 | 3.4 | 9.6 |

EXAMPLE 45

When tested by the standard method described hereinabove, compounds of the invention inhibit growth of microorganisms in concentrations of 1 to 100 milligrams/liter as shown in the following table.

TABLE VI

| Compound (Example No.) | SS | SA | BS | EC | PA | MP | HV |
|---|---|---|---|---|---|---|---|
| 18 | − | − | + | − | − | − | − |
| 19 | − | + | + | + | − | − | + |
| 44 | − | + | + | + | − | − | + |
| 1 | − | + | + | + | − | − | + |
| 16 | + | + | + | + | − | − | + |
| 17 | + | − | + | + | − | − | + |
| 20 | − | + | + | + | − | − | + |
| 21 | + | + | + | + | − | − | + |
| 22 | + | + | + | + | + | + | + |
| 25 | + | − | + | + | − | − | + |
| 24 | + | + | + | + | + | − | + |
| 5 | − | − | + | + | − | − | + |
| 6 | − | + | + | + | + | − | + |
| 4 | − | + | + | + | − | − | + |
| 23 | + | + | + | + | − | − | + |
| 34 (ester) | + | + | + | + | + | + | + |
| 34 (acid) | + | + | + | + | + | + | + |
| 26 | + | + | + | + | − | − | + |
| 37 (ester) | − | − | + | − | − | − | − |
| 37 (acid) | + | + | + | + | + | + | + |
| 38 (acid) | − | + | + | + | − | − | + |
| 39 (acid) | + | − | + | + | + | + | + |
| 39 (ester) | + | − | − | + | + | − | − |
| 40 (acid) | + | + | + | + | + | + | + |
| 41 (ester) | − | + | + | + | − | − | + |
| 41 (acid) | − | + | + | + | − | − | + |
| 42 (ester) | − | − | + | − | − | − | − |
| 42 (acid) | + | + | + | + | + | + | + |
| 43 (acid) | + | + | + | + | − | − | + |

+ active
− inactive

SS = Streptococcus Sp
SA = Staphylococcus aureus
BS = Bacillus Subtilus
EC = Escherichia coli
PA = Pseudmonas aeruginosa
MP = Mima polymorpha
HV = Herellea vaginicola

What is claimed is:
1. A method for inhibiting the growth of bacteria which comprises applying to said bacteria a bactericidally effective amount of a compound of the formula

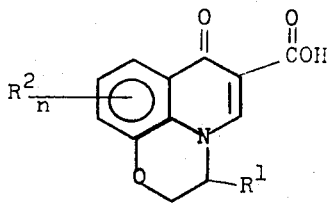

wherein $R^1$ is hydrogen or lower alkyl, $R^2$ is lower alkyl, lower alkoxy, halogen or nitro, n is zero to three, and when $R^2$ is nitro, $R^1$ is methyl or ethyl; or a pharmaceutically acceptable salt thereof.

2. The method according to claim 1 wherein the compound is 10-chloro-2,3-dihydro-3-methyl-7-oxo-7H-pyrido [1,2,3-de]-1,4-benzoxazine-6-carboxylic acid.

3. The method according to claim 1 wherein the compound is 2,3-dihydro-9-fluoro-3-methyl-7-oxo-7H-pyrid. [1,2,3-de]-1,4-benzoxazine-6-carboxylic acid.

4. The method according to claim 1 wherein the compound is 9-chloro-2,3-dihydro-3-methyl-7-oxo-7H-pyrido [1,2,3-de]-1,4-benzoxazine-6-carboxylic acid.

5. The method according to claim 1 wherein the compound is 10-chloro-2,3-dihydro-3,8-dimethyl-7-oxo-7H-pyrido[1,2,3-de]-1,4-benzoxazine-6-carboxylic acid.

6. The method according to claim 1 wherein the compound is 2,3-dihydro-3,10-dimethyl-7-oxo-7H-pyrido[1,2,3-de]-1,4-benzoxazine-6-carboxylic acid.

7. The method according to claim 1 wherein the compound is 9-chloro-2,3-dihydro-3,10-dimethyl-7-oxo-7H-pyrido[1,2,3-de]-1,4-benzoxazine-6-carboxylic acid.

8. The method according to claim 1 wherein the compound is 2,3-dihydro-7-oxo-3,8,10-trimethyl-7H-pyrido [1,2,3-de]-1,4-benzoxazine-6-carboxylic acid.

9. The method according to claim 1 wherein the compound is 2,3-dihydro-3,9-dimethyl-7-oxo-7H-pyrido [1,2,3-de]-1,4-benzoxazine-6-carboxylic acid.

10. A method for inhibiting the growth of bacteria comprising applying to said bacteria a composition comprising a conventional pharmaceutical carrier and a bactericidally effective amount of a compound of the formula

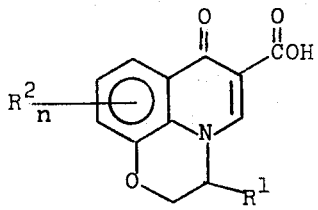

wherein $R^1$ is hydrogen or lower alkyl, $R^2$ is lower alkyl. lower alkoyx, halogen or nitro, n is zero to three, and when $R^2$ is nitro, $R^1$ is methyl or ethyl; or a pharmaceutically acceptable salt thereof.

* * * * *